United States Patent [19]

Chang et al.

[11] Patent Number: 4,621,164

[45] Date of Patent: Nov. 4, 1986

[54] HYDROCARBON PRODUCTION

[75] Inventors: Martin M. Chang; George T. Tsao, both of West Lafayette, Ind.; Allen W. Anderson, Waterloo, Wis.

[73] Assignee: Purdue Research Foundation, West Lafayette, Ind.

[21] Appl. No.: 747,236

[22] Filed: Jun. 21, 1985

Related U.S. Application Data

[63] Continuation of Ser. No. 483,118, Apr. 8, 1983, abandoned, which is a continuation-in-part of Ser. No. 414,784, Sep. 3, 1982, abandoned.

[30] Foreign Application Priority Data

Dec. 14, 1981 [CA] Canada ................................... 392210

[51] Int. Cl.$^4$ .......................... C07C 1/00; C07C 11/20
[52] U.S. Cl. .................................... 585/733; 585/408; 585/640
[58] Field of Search ........................ 585/640, 733, 408

[56] References Cited

U.S. PATENT DOCUMENTS 3,702,886  11/1972  Argauer et al. .
3,894,107   7/1975  Butter et al. .
3,928,483  12/1975  Chang et al. .
4,079,095   3/1978  Givens et al. .
4,083,889   4/1978  Caeser et al. .
4,138,440   2/1979  Chang et al. .
4,278,565   7/1981  Chen et al. .
4,296,266  10/1981  Wunder et al. .

OTHER PUBLICATIONS

Anderson et al., *Journal of Catalysis*, 58, 114–130 (1979).
Meisel et al., *Chemtech*, 6, 86–89 (1976).
Chang et al., *Journal of Catalysis*, 47, 249–259 (1977).
*Encyclopedia of Chemical Technology*, 3rd Ed (1981), New York: John Wiley, 11, 678–680.
Rajadhyaksha et al., *Journal of Catalysis*, 63, 510–514 (1980).
Oudejans et al., "Conversion of Ethanol Over Zeolite H-ZSM-5 in the The Presence of Water," *Applied Catalysis*, 3, 109–115 (1982).

*Primary Examiner*—Curtis R. Davis
*Attorney, Agent, or Firm*—Barnes & Thornburg

[57] ABSTRACT

A process for converting ethanol to gasoline-boiling-range hydrocarbons by contact in the vapor phase at dehydrating temperature with a bifunctional zeolite catalyst in the presence of an equimolar proportion of water. The catalyst induces simultaneous dehydration of the ethanol to reactive intermediates and recombination to a spectrum of hydrocarbons in the $C_1$ to $C_{10}$ range. Higher and lower proportions of water lead to higher yields of gaseous hydrocarbons.

6 Claims, No Drawings

HYDROCARBON PRODUCTION

This application is a continuation of application Ser. No. 483,118 filed Apr. 8, 1983, now abandoned, which application is a continuation-in-part of our application Ser. No. 414,784 filed Sept. 3, 1982, now abandoned.

This invention relates to an improvement in the production of gasoline-boiling-range hydrocarbons from ethanol, e.g., from fermentation-derived ethanol, and more particularly to a method for maximizing the production of liquid hydrocarbons from ethanol.

It has been known for some time that simple oxygenated organic compounds can be converted in some degree into hydrocarbons of gasoline-boiling range. Meisel et al, *Chem. Technol.*, 6, 86 (1976); Chang et al, *J. Catalysis*, 47, 249 (1977). Such a conversion is described in U.S. Pat. No. 3,894,107, using a zeolite catalyst designated as ZSM-5 (U.S. Pat. No. 3,702,886), and in U.S. Pat. No. 3,928,483. Although both patents assert that $C_1$ to $C_3$ alcohols can be converted according to the described method, their experimental showing relates only to methanol; and indeed there has been no successful application of the method to ethanol.

The only lower alcohol manufactured on a commercial scale from biomass is ethanol. From biomass to methanol, the most logical process is the one similar to the famous Fischer-Tropsch technique which first converts a carbonaceous substance to carbon monoxide and then adds two moles of hydrogen to generate the methanol, $CH_3OH$. This type of process is energy-intensive. It has been estimated that to go through the biomass-to-methanol-to-gasoline conversion with the ZSM-5 process, the production cost alone could amount to around $20/MMBtu. (Ergun, Lawrence Berkeley Laboratory Report, LBL-10456, MC-61, 1980). This makes it one of the most energy-deficient conversion processes.

The major difficulty encountered in the processing of ethanol to hydrocarbons is that the conversion generally stops at the production of ethylene, and if any higher hydrocarbons happen to form, the yield is poor and not reproducible. The catalyst life time in the treatment of ethanol is also very short compared with the treatment of methanol. For example, when the so-called protonated ZSM-5 zeolite catalyst was used under conditions set forth in the previously mentioned patents, ethanol was predominantly converted to ethylene. With the so-called acid-processed zeolite, ZSM-5H, ethanol was converted to a spectrum of higher hydrocarbons similar to that from methanol conversion, but the catalyst lifetime was considerably shortened to a time span of less than 5 hours, as compared to several tens of hours in the conversion of methanol (see Rojadhyaksha et al, *Journal of Catalysis*, 63, 510, 1980). Other workers in related fields have experienced similar frustrations with zeolite catalysts in ethanol conversion (Anderson et al, *Journal of Catalysis*, 58, 114 (1979)).

Even in the methanol-to-gasoline system, there are practical problems. First, the degree of conversion is essentially 100%, but the overall reaction is highly exothermic, so that heat dissipation is a problem, which has so far been solved only by going to a two-stage reaction with different catalysts. Secondly, the end product exhibits a broad distribution of carbon chains which can basically be divided into a gaseous product containing $C_1$ to $C_4$ hydrocarbons and a liquid product of $C_5$ to $C_{10}$ hydrocarbons, and no way is known to control the product distribution between these two categories.

Notwithstanding the large amount of work reported in the prior art, it is quite clear that the chemical practitioner still has no satisfactory way to convert ethanol into hydrocarbons of gasoline boiling range.

It is therefore an object of this invention to provide an improved process for converting ethyl alcohol to valuable hydrocarbon fuels.

An additional object is to provide a novel process for the economical conversion of fermentation-derived ethanol into hydrocarbon fuel.

A further object of the invention is to provide a novel process for converting ethanol into liquid hydrocarbons which is free of heat dissipation problems.

A still further object is to provide a means to effectively control the product distribution in the conversion of ethanol into liquid hydrocarbons.

These and other objects of the invention will become apparent from the present specification and claims.

From the stoichiometry involved in the present invention, it will be apparent that two principal reactions are involved—viz., the dehydration of ethanol over the zeolite catalyst, and the recombination of the resulting hydrocarbon intermediate(s) to form the desired liquid hydrocarbons.

One important aspect of the invention lies in the discovery that the desired reactions are favored by inclusion of a substantial quantity of water as a co-reactant in the reaction mixture. The proportion of water may range from about 10 wt % to about 70 wt % (hereinafter all expressions in percent and parts are on a weight basis unless otherwise specified) of the ethanol-water mixture depending on the desired product distribution. Optimally, an equimolar proportion of water to ethanol should be added to obtain the best product distribution in terms of maximizing the yield of gasoline-boiling-range liquid fuel. The water may be added to the reaction system as pressurized steam prior to entering the catalytic reactor, or liquid water may be premixed with the alcohol feed (e.g., in the form of the ethanol-water azeotrope, or the aqueous ethanol distillate from fermented mash). The operating conditions may otherwise closely parallel the conventional dehydration-recombination treatment of methanol with zeolite catalyst, namely, reaction temperatures in the range of 300° to 500° C., preferably 400° to 450° C.; pressures in the range of 1 to 100 atmospheres, preferably 2 to 25 atmospheres, and feed rates in the range of 0.5 to 50 liquid hourly space velocity, preferably 1 to 10.

In order to achieve the improved results of the invention, we find that there must be a sufficient proportion of water molecules in the catalyst zone. A "sufficient proportion," as we have found, is about one molecule of water per methylene group, although improved results are obtainable in diminishing degrees at lower and higher proportions of water. We do not know the mechanism whereby our improved result is obtained with ethanol; but having observed the improved result, we are led to some interesting speculations from the prior art's success with methanol. With pure methanol as a feedstock, an equimolar quantity of water is generated by the dehydration step, yielding a total water content of about 56% in the reaction product mixture at the completion of the reaction. When pure ethanol is used, however, the number of water molecules generated internally per methylene groups as a result of the dehydration reaction is half of that using methanol. The resulting final water content with ethanol is thus only 39%; and as the art shows, the results are a short catalyst life and little or no production of any hydrocarbons except ethylene. It is an important discovery of the present invention that the additional water introduced into the reaction zone with ethanol functions in some way to produce our observed results.

A second aspect of the invention lies in adjusting the water content of the ethanol feed as a means of controlling the product distribution. It has been observed that water added in excess of the equimolar ratio shifts the product distribution toward gaseous products, while nevertheless allowing the reaction to be completed in terms of the alcohol-to-hydrocarbon conversion. Thus, the ratio of gaseous to liquid products can be controlled by adjustment of the amount of water added to the ethanol feed while other parameters remain unchanged. A higher water content (>40%) in the ethanol feed yields more gaseous hydrocarbon at the expenses of the liquid components, and a lower water content (<40%) gives considerably more liquid hydrocarbons. The maximum conversion to aromatic hydrocarbons takes place at the equimolar concentration, i.e., 28% of water. This finding provides additional means of process control to reach a desired product composition. If market conditions are such that propane or other gaseous hydrocarbons are in demand, we can shift the process parameters very quickly to meet the market demand without adding any extra equipment or altering the basic production process itself. Furthermore, we do not find any appreciable deterioration in catalytic activity in runs exceeding 20 hours in duration at high flow rates.

It is surprising and indeed quite unexpected that our hydrolytic dehydration-recombination of ethanol works as well as it does in view of the common experience that an increased amount of water and/or time of contact of zeolite with water accelerates the loss of catalytic activity (U.S. Pat. No. 3,894,107, column 4, line 14).

As another advantage, our improved process essentially eliminates the heat dissipation problem encountered in the zeolite-methanol conversion process of the prior art. The exothermic heat of reaction for ethanol-to-gasoline conversion is small when compared to that of methanol. At an average value of 450 Btu per pound of hydrocarbons produced from pure ethanol, the amount of heat to be dissipated is about 3.7 times smaller than that from methanol. With water added either directly to the catalytic reactor or supplied as a co-component in the ethanol feed, the heat required to bring this amount of water up to the reaction temperature alone will take up all the exothermic reaction heat. Local overheating within the crystalline sites of the zeolite catalyst is also avoided because the excess amount of steam acts to dilute and dissipate the heat.

In operating the process of our invention, an ethanol feedstock is made up to the desired proportion of water, and is conveyed directly through a preheater, a vaporizer, and a superheater into the catalytic reaction zone. A substantially pure ethanol feed, for example, would require addition of water to a level of 28% of the total mixture for an equimolar ratio, leading to a 1:1 ratio of methylene to water in the reaction product. The overall chemical reaction of the water co-catalyzed dehydration-recombination of ethanol can be represented by the following equation:

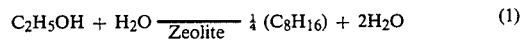

$$C_2H_5OH + H_2O \xrightarrow{\text{Zeolite}} \tfrac{1}{8}(C_8H_{16}) + 2H_2O \quad (1)$$

Here the $(C_8H_{16})$ represents the average formula of a spectrum of hydrocarbons ranging from $C_1$ to $C_{10}$. In this reaction, water is apparently participating in the reaction to promote the overall conversion. Since it is not consumed in the reaction, the role of the water molecule can be regarded as catalytic, according to the basic definition of catalysis chemistry. At the end of the reaction, this catalytic amount of water, along with the newly generated water from the dehydration phase of the reaction, is easily condensed to the liquid state and separated from the hydrocarbon products. The desired catalytic amount of water can be pumped back to the reactor, avoiding any need to supply additional water with the ethanol feed. If the desired proportion of gaseous to liquid products is different from the gasoline range, the quantity of circulating water may be shifted accordingly. The desired water level can be determined by interpolation from a predetermined curve relating the water content of the total feed to the product composition.

In recognition of the double capability of the natural zeolite catalysts, such as ZSM-5, the catalyst can be regarded as bifunctional. The first of these functions is dehydration. Water is stripped off the ethanol to give ethylene as the most likely intermediate. The second of these functions is recombination of the intermediate ethylene to form a complete spectrum of hydrocarbons including most, if not all, of the molecular moieties of the $C_1$ to $C_{10}$ family. These molecular moieties fall into the classes of gaseous aliphatic hydrocarbons ($C_1$-$C_4$), liquid aliphatics ($C_5$-$C_{10}$), and aromatics from $C_6$ to $C_{10}$.

It will be apparent that "recombination" is not a simple reaction, but rather a complex series of reactions, including oligomerization, cyclization, dehydrocyclization (the so-called "aromatization"), isomerization, cracking, and hydrogenation.

Illustrative catalysts include the cited ZSM-5 type of catalyst in either cationic form such as the sodium, hydrogen, or ammonium forms as described in U.S. Pat. No. 3,702,886, the zeolites ZSM-12, ZSM-21, ZSM-35, ZSM-38, and TEA Mordenite as described in U.S. Patent 3,928,483, and Silicalite as described by Flanigen et al, Nature, 271 (5645), p. 512 (1978). The catalyst by itself, however, is not a part of the claimed invention, despite its importance in carrying out the desired reaction. By the same token, the specific cationic form of (or pretreatment to) the zeolite catalyst is also not a part of the present invention.

A practical source of feedstock for our process is ethanol as currently produced by fermentation of biomass substances. The concentration of ethanol in the fermentation broth is ordinarily about 8% to 12%, and the rest is mostly water. By a simple distillation of the broth, a condensate can easily be obtained comprising 72% ethanol and 28% water. This is a perfect feed for producing the optimum gasoline-boiling range product. For hydrocarbon products of other than gasoline-boiling range, the adjustment of the required water level in the feedstock can be made at the distillation stage as desired. Numerous modifications of this nature may be made having additional advantages of energy and capital savings in the actual production process which do not depart from the spirit and scope of the present invention.

By the same token, when the ethanol employed comes from a synthetic process, such as U.S. Pat. No. 2,579,601, the crude ethanol condensate contains a substantial amount of water (about 40 to 70%), depending upon the conditions employed in the synthesis, together with some minor quantity of simple oxygenates such as ethers, aldehydes, etc. Through simple distillation, the water level of the condensate can be adjusted to 28% to provide the desirable feed for the hydrolytic dehydration-recombination process. The presence of the minor quantities of simple oxygenates other than alcohol does not interfere with the overall production of hydrocarbons.

The following examples of the invention are submitted as illustrative only, and not by way of limitation.

EXAMPLE 1

In this example, aqueous ethanol containing 28% water was vaporized and passed through a column reactor packed with ZSM-5H zeolite catalyst under the following experimental conditions: liquid hourly space velocity 8.0, temperature 400° C., inlet pressure 14 atmospheres, outlet pressure 1 atmosphere, and total internal water proportion 56%. The liquid hydrocarbon products were collected over Dry Ice-methanol bath which maintained a temperature of −25°±5° C. The relative product distributions of the liquid hydrocarbons, analyzed by gas chromatography, are listed in Table 1. For comparison purposed, pure methanol (without added water) was processed by the same procedure and under the same conditions. For further comparison, the gas chromatogram of a commercial gasohol purchased at a retail gasoline station is also given in Table 1. Although the product distributions obtained from methanol and from aqueous ethanol bear some similarity, it is apparent that the product obtained from aqueous ethanol more closely resembles commercial gasohol.

TABLE 1

| Peaks | Identified Hydrocarbons | Relative Distribution (% Area) | | |
|---|---|---|---|---|
| | | Methanol | Ethanol | Gasohol |
| 1 | | 3.28 | .61 | 1.65 |
| 2 | n-Pentane | 10.76 | 5.59 | 7.00 |
| 3 | | 6.61 | 5.09 | 6.54 |
| 4 | n-Hexane | 7.00 | 6.75 | 6.10 |
| 5 | | 4.98 | .17 | — |
| 6 | | 1.42 | 5.10 | 3.93 |
| 7 | | 1.31 | 2.00 | 7.64 |
| 8 | | 3.60 | 1.41 | — |
| 9 | n-Heptane | 2.69 | 5.51 | 8.35 |
| 10 | | 1.33 | 3.80 | 3.91 |
| 11 | | 1.14 | 2.49 | 6.08 |
| 12 | n-Octane | .15 | 1.84 | 1.69 |
| 13 | | .13 | .51 | — |
| 14 | | 1.25 | .29 | — |
| 15 | | .57 | 2.02 | 1.40 |
| 16 | | 1.07 | 1.33 | — |
| 17 | | .42 | 2.12 | 1.32 |
| 18 | n-Nonane | .54 | 1.00 | .39 |
| 19 | | .11 | 1.36 | .15 |
| 20 | | .21 | .27 | .17 |
| 21 | | .39 | .45 | — |
| 22 | | .22 | .79 | .58 |
| 23 | n-Decane | .16 | 1.41 | .30 |
| 24 | Benzene | 1.69 | 1.41 | 1.82 |
| 25 | Ethanol | — | .14 | 6.44 |
| 26 | | .35 | .32 | — |
| 27 | | .17 | .23 | .12 |
| 28 | | .45 | .34 | — |
| 29 | Toluene | 10.47 | 8.75 | 9.10 |
| 30 | | .41 | .38 | .30 |
| 31 | Xylene | 1.76 | 1.66 | 1.68 |
| 32 | Xylene | 2.68 | 3.02 | 2.33 |
| 33 | Xylene | 16.89 | 13.20 | 8.89 |
| 34 | | — | .39 | .29 |
| 35 | Trimethyl Benzene | 5.50 | 3.49 | 3.85 |
| 36 | Trimethyl Benzene | 4.00 | 4.10 | 2.41 |
| 37 | Trimethyl Benzene | 6.29 | 10.61 | 4.94 |

TABLE 1-continued

| Peaks | Identified Hydrocarbons | Relative Distribution (% Area) | | |
|---|---|---|---|---|
| | | Methanol | Ethanol | Gasohol |
| 38 | | — | — | 0.62 |
| Total Peak Area | | 100.00 | 100.02 | 99.99 |
| % Aliphatics ($C_5$-$C_{10}$) | | 49.4 | 52.1 | 57.2 |
| % Aromatics | | 50.6 | 47.9 | 36.4 |

EXAMPLES 2–7

In these examples, methanol, 90% ethanol, 72% ethanol, 60% ethanol, 50% ethanol, and 30% ethanol were fed through the column reactor packed with ZSM-5H catalyst at a feed rate of 8 liquid hourly space velocity, inlet pressure 14 atm, outlet pressure 1 atmosphere, and temperature 400° C. The hydrocarbon products were determined in three categories as listed in Table 2. It was observed that essentially all alcohols were converted to hydrocarbons, and that with ethanol the yield of gaseous product was increased at the expense of the liquid product at water levels above equimolar.

TABLE 2

| Example No. | 2 | 3 | 4 | 5 | 6 | 7 |
|---|---|---|---|---|---|---|
| Alcohol Concentration % | 100 | 90 | 72 | 60 | 50 | 30 |
| Alcohol Species | Methyl | Ethyl | Ethyl | Ethyl | Ethyl | Ethyl |
| Alcohol Conversion % | 100 | 99.7 | 99.7 | 99.5 | 99.6 | 99.6 |
| Water Recovery %* | 96 | 93 | 95 | 97 | 93 | 91 |
| Major Gaseous Product Hydrocarbons Formed % | $C_3H_8$ | $C_3H_8$ | $C_3H_8$ | $C_3H_8$ | $C_3H_8$ | $C_3H_8$ |
| Gaseous ($C_1$-$C_4$) | 31 | 32 | 31 | 42 | 58 | 84 |
| Liquid, Aliphatics | 35 | 45 | 34 | 34 | 27 | 10 |
| Liquid, Aromatics | 34 | 24 | 35 | 24 | 15 | 6 |

*Water recovered divided by the theoretical yield of water according to Equation 1.

EXAMPLE 8

In a further test, a mixture of 72% ethanol and 28% water was passed over a ZSM-5 catalyst (designation, ZSM-5H(2)) in hydrogen ion form at weight hourly space velocity 4, reaction temperature 370° C., and inlet pressure 3 atm. The extent of conversion to hydrocarbons was 100%, of which 33% was $C_1$-$C_4$ gaseous hydrocarbons and 67% liquid hydrocarbons (combined aliphatics and aromatics).

EXAMPLE 9

In a further test, a mixture of 72% ethanol and 28% water was passed over a zeolite catalyst (designation, Silicalite Si-H(1)) obtained by calcining the ammonium form. The liquid hourly space velocity was 8, the reaction temperature 450° C., and the inlet pressure 34 atm. The extent of conversion to hydrocarbons was 100%, of which 41% was $C_1$-$C_4$ gaseous hydrocarbons and 59% liquid hydrocarbons (combined aliphatics and aromatics).

While we have described our invention with reference to certain feed stocks and operating conditions and procedures, it will be apparent to those skilled in this art that numerous departures may be made therefrom without departing from the spirit of the invention. The zeolite catalysts are well known and generally available; and while the results will vary with individual catalysts, the general class of zeolite catalysts are useful in the invention. Elevated pressures are preferred in principle, to increase the tendency of the alkylene intermediates to polymerize, but the pressure is not critical and may range upward from 1 to 100 atmospheres or more, limited ony by the economic balance of equipment cost. The temperature will ordinarily range from about 300° to about 500° C., being limited on the lower side only to the temperatures necessary to cause dehydration of ethanol by the catalyst employed, and on the high side to temperatures that do not produce unacceptable carbonization of the catalyst. The space velocity can be around 0.5 to 15 (liquid hourly basis), more or less, depending on the dehydration activity of the catalyst employed. The reactor can be of fixed-bed or fluidized-bed type. All such variants lie within the spirit and scope of the invention.

What is claimed is:

1. A process for converting an aqueous ethanolic broth to liquid hydrocarbons predominately of gasoline-boiling range which comprises adjusting the ethanol content of said broth to about 72% by weight and passing said broth in the vapor phase over a zeolite catalyst at a temperature between about 400° and 450° C., an hourly liquid space velocity between about 0.5 and about 15, and a pressure between about 2 and about 25 atmospheres.

2. In a process for converting an ethanol feed stream to a hydrocarbon product stream at elevated temperature and pressure in the presence of a zeolite having catlytic activity, the improvement which comprises adding water to the ethanol feed stream in an amount sufficient to provide an aqueous ethanol feed stream having a water content of about 28 weight percent to about 70 weight percent to minimize loss of zeolite catalytic activity and to control distribution of gaseous and liquid hydrocarbon products in the hydrocarbon product stream.

3. A method for controlling the distribution of gaseous and liquid hydrocarbon products produced by the reaction of an ethanol feed stream in the presence of a zeolite catalyst at elevated temperature and pressure, which method comprises adding water to the ethanol feed stream in an amount sufficient to provide an aqueous alcohol feed stream having a water content of between about 28 weight percent and about 70 weight percent wherein production of gaseous hydrocarbon products is favored by feed stream water content greater than 40% by weight and production of liquid hydrocarbon products is favored by feed stream water content less than 40% by weight.

4. The method of claim 3 wherein water is added to the ethanol feed stream in an amount sufficient to provide an equi-molar proportion of water and ethanol wherein the yield of gasoline-boiling-range hydrocarbon products is maximized.

5. The method of claim 3 wherein the water content of the ethanol feed stream is adjusted to greater than about 40% by weight to favor production of gaseous hydrocarbon products.

6. The method of claim 3 wherein the water content of the ethanol feed stream is adjusted to less than 40% by weight to favor production of liquid hydrocarbons.

* * * * *